United States Patent
Dickerson

(10) Patent No.: US 6,199,239 B1
(45) Date of Patent: Mar. 13, 2001

(54) TOOTHBRUSH WITH AUDIBLE REMINDER MECHANISM

(76) Inventor: Herbert A. Dickerson, Rte. 2, Box 144A, Sallis, MS (US) 39160

( * ) Notice: Subject to any disclaimer, the term of this patent is extended or adjusted under 35 U.S.C. 154(b) by 0 days.

(21) Appl. No.: 09/388,426

(22) Filed: Sep. 1, 1999

(51) Int. Cl.⁷ .................................................. A46B 15/00
(52) U.S. Cl. ........................... 15/105; 15/22.1; 15/167.1; 15/DIG. 1; 320/114
(58) Field of Search ........................ 15/22.1, 105, 167.1, 15/DIG. 1; 320/114

(56) References Cited

U.S. PATENT DOCUMENTS

| | | |
|---|---|---|
| 4,341,230 | 7/1982 | Siahou .............................. 15/167.1 X |
| 4,698,869 * | 10/1987 | Mierau et al. ......................... 15/22.1 |
| 4,866,807 | 9/1989 | Kreit et al. .............................. 15/105 |
| 5,044,037 | 9/1991 | Brown ..................................... 15/105 |
| 5,259,086 | 11/1993 | Fong ....................................... 15/105 |
| 5,561,881 * | 10/1996 | Klinger et al. ......................... 15/22.1 |
| 5,572,762 | 11/1996 | Scheiner ................................. 15/105 |
| 5,673,451 | 10/1997 | Moore et al. ........................... 15/105 |

FOREIGN PATENT DOCUMENTS

3149233 * 4/1983 (DE) ...................................... 15/105

* cited by examiner

*Primary Examiner*—Mark Spisich
(74) *Attorney, Agent, or Firm*—Joseph N. Breaux

(57) ABSTRACT

A toothbrush system that includes an audible reminder mechanism for reminding individuals to brush their teeth. The audible reminder mechanism is triggered by sound recognition circuit that in the exemplary embodiment is programmed to recognize the sound of running water. The toothbrush system also includes a user insertable electronic music chip insertable through a chip insertion opening formed through a side of an elongated gripping portion of the toothbrush handle.

1 Claim, 3 Drawing Sheets

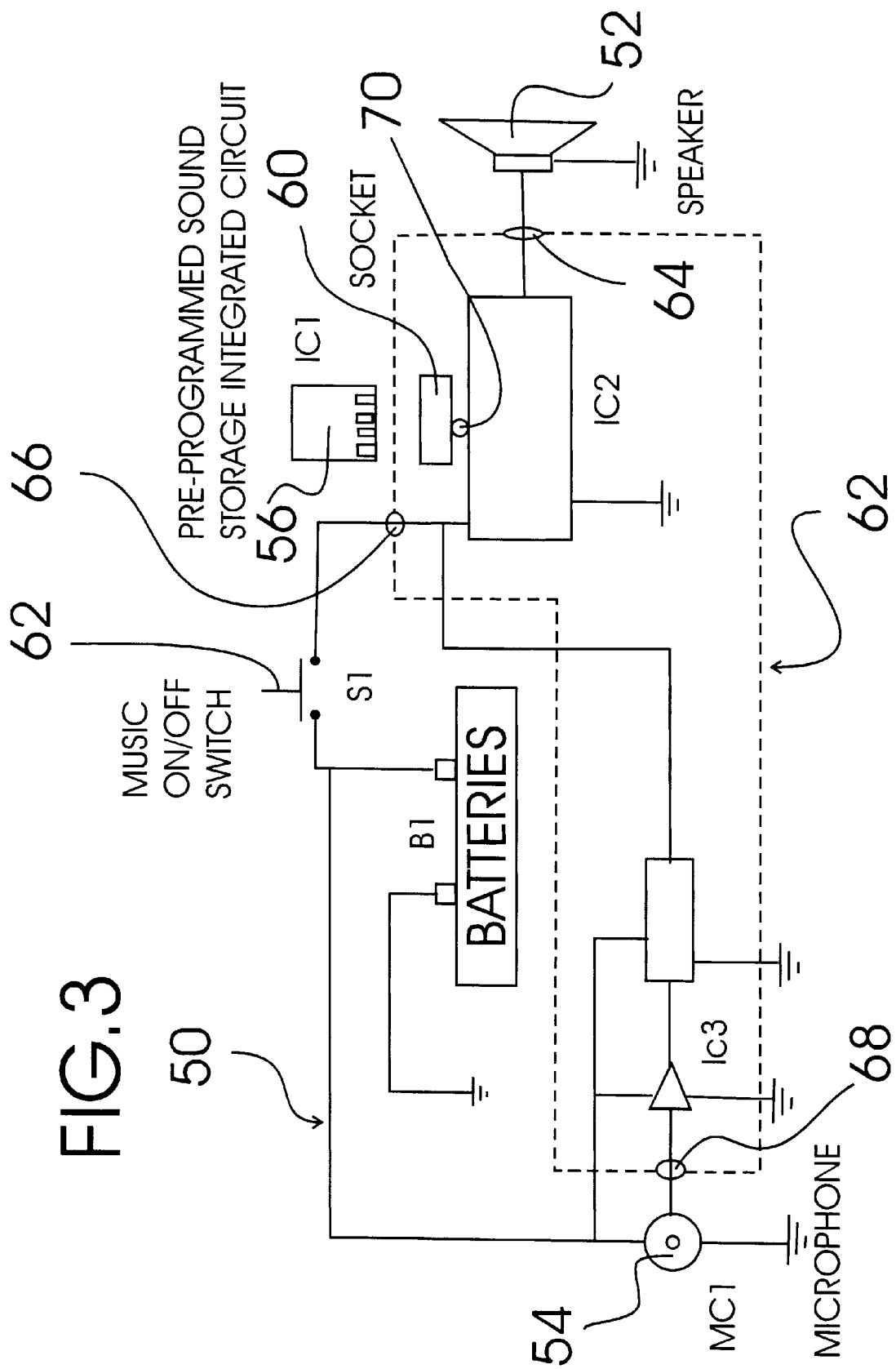

TOOTHBRUSH WITH AUDIBLE REMINDER MECHANISM

TECHNICAL FIELD

The present invention relates to oral hygiene products and more particularly to a toothbrush with audible reminder mechanism that includes a brush assembly and a recharging base; the recharging base including a brush assembly receiving cavity having two charger contacts provided at the bottom thereof and a hook slot in connection with the brush assembly receiving cavity; the brush assembly including a handle assembly and a removable brush assembly having a brush head attached shaft portion having a shaft end that fits into a receiving cavity at a top end of the handle assembly; the handle assembly including a molded plastic housing having a detachable bottom cap assembly and a elongated gripping portion; the detachable bottom cap assembly being detachably connectable to the elongated gripping portion and including a pair of spaced recharging contacts and a hanger hook extending out past a side of the elongated gripping portion; the bottom cap assembly being insertable into the brush assembly receiving cavity such that the two charger contacts provided at the bottom of the brush receiving cavity electrically connect with the two recharging contacts of the bottom cap assembly and the hanger hook is positioned through the hook slot; the elongated gripping portion housing a rechargeable battery pack in electrical connection with the pair of spaced recharging contacts and a reminder mechanism including a sealed output speaker, a sealed microphone, a user insertable electronic music chip insertable through a chip insertion opening formed rough the side of the elongated gripping portion, an on/off switch and a music generating circuit having a speaker output in connection with the output speaker, a power input in connection the on/off switch, a sound detector microphone input in connection with the microphone, and a sound data input in connection with the user insertable electronic music chip; the music generating circuit retrieving sound data from the user insertable electronic music chip and generating a music output signal to the speaker after a predetermined sound is detected at the sound detector microphone input.

BACKGROUND ART

Many individuals, particularly small children, forget to brush. It would be desirable, therefore, to have a toothbrush system that included an audible reminder mechanism for reminding individuals to brush their teeth. Because the reminder mechanism would be most effective when the person to be reminded was in the room, it would be further benefit if the reminder mechanism was triggered by a sound generated when a person is present. Because the sound of running water is typically initiated by a person activating a valve or the like, it would be desirable if the reminder mechanism was triggered by the sound of running water.

GENERAL SUMMARY DISCUSSION OF INVENTION

It is thus an object of the invention to provide a toothbrush with audible reminder mechanism that includes a brush assembly and a recharging base; the recharging base including a brush assembly receiving cavity having two charger contacts provided at the bottom thereof and a hook slot in connection with the brush assembly receiving cavity; the brush assembly including a handle assembly and a removable brush assembly having a brush head attached shaft portion having a shaft end that fits into a receiving cavity at a top end of the handle assembly; the handle assembly including a molded plastic housing having a detachable bottom cap assembly and a elongated gripping portion; the detachable bottom cap assembly being detachably connectable to the elongated gripping portion and including a pair of spaced recharging contacts and a hanger hook extending out past a side of the elongated gripping portion; the bottom cap assembly being insertable into the brush assembly receiving cavity such that the two charger contacts provided at the bottom of the brush receiving cavity electrically connect with the two recharging contacts of the bottom cap assembly and the hanger hook is positioned through the hook slot; the elongated gripping portion housing a rechargeable battery pack in electrical connection with the pair of spaced recharging contacts and a reminder mechanism including a sealed output speaker, a sealed microphone, a user insertable electronic music chip insertable through a chip insertion opening formed through the side of the elongated gripping portion, an on/off switch and a music generating circuit having a speaker output in connection with the output speaker, a power input in connection the on/off switch, a sound detector microphone input in connection with the microphone, and a sound data input in connection with the user insertable electronic music chip; the music generating circuit retrieving sound data from the user insertable electronic music chip and generating a music output signal to the speaker after a predetermined sound is detected at the sound detector microphone input.

Accordingly, a toothbrush with audible reminder mechanism is provided. The toothbrush with audible reminder mechanism includes a brush assembly and a recharging base; the recharging base including a brush assembly receiving cavity having two charger contacts provided at the bottom thereof and a hook slot in connection with the brush assembly receiving cavity; the brush assembly including a handle assembly and a removable brush assembly having a brush head attached shaft portion having a shaft end that fits into a receiving cavity at a top end of the handle assembly; the handle assembly including a molded plastic housing having a detachable bottom cap assembly and a elongated gripping portion; the detachable bottom cap assembly being detachably connectable to the elongated gripping portion and including a pair of spaced recharging contacts and a hanger hook extending out past a side of the elongated gripping portion; the bottom cap assembly being insertable into the brush assembly receiving cavity such that the two charger contacts provided at the bottom of the brush receiving cavity electrically connect with the two recharging contacts of the bottom cap assembly and the hanger hook is positioned through the hook slot; the elongated gripping portion housing a rechargeable battery pack in electrical connection with the pair of spaced recharging contacts and a reminder mechanism including a sealed output speaker, a sealed microphone, a user insertable electronic music chip insertable through a chip insertion opening formed through the side of the elongated gripping portion, an on/off switch and a music generating circuit having a speaker output in connection with the output speaker, a power input in connection the on/off switch, a sound detector microphone input in connection with the microphone, and a sound data input in connection with the user insertable electronic music chip; the music generating circuit retrieving sound data from the user insertable electronic music chip and generating a music output signal to the speaker after a predetermined sound is detected at the sound detector microphone input.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein:

FIG. 3 is a schematic diagram of the reminder mechanism.

EXEMPLARY MODE FOR CARRYING OUT THE INVENTION

Figure 1:
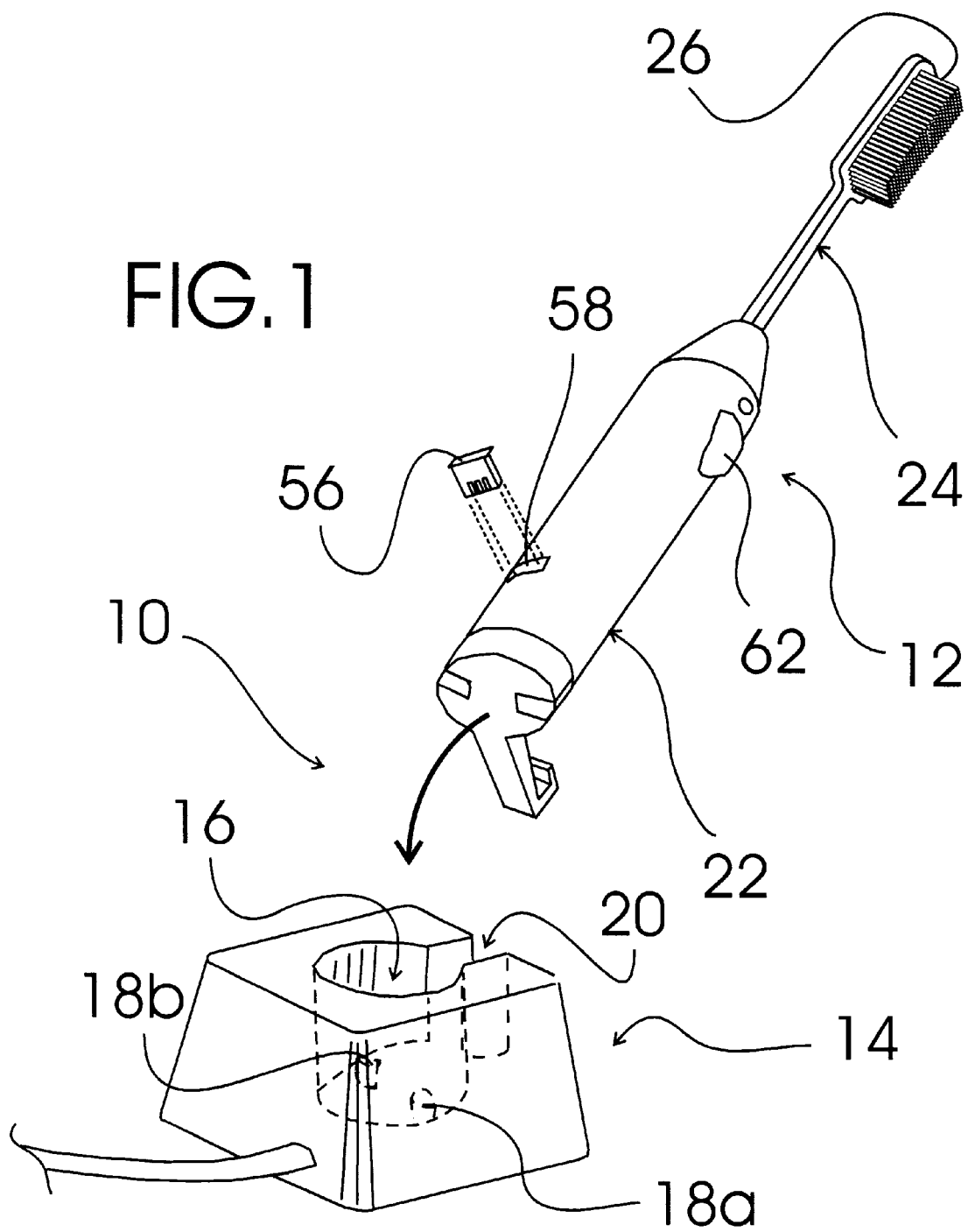
FIG. 1 is a perspective view of an exemplary embodiment of the toothbrush with audible reminder mechanism of the present invention showing the brush assembly and the recharging base; the recharging base including a brush assembly receiving cavity having two charger contacts provided at the bottom thereof and a hook slot in connection with the brush assembly receiving cavity; the brush assembly including a handle assembly and a removable brush assembly having a brush head attached shaft portion having a shaft end that fits into a receiving cavity at a top end of the handle assembly; the handle assembly including a molded plastic housing having a detachable bottom cap assembly and a elongated gripping portion; the detachable bottom cap assembly being detachably connectable to the elongated gripping portion and including a pair of spaced recharging contacts and a hanger hook extending out past a side of the elongated gripping portion; the bottom cap assembly being insertable into the brush assembly receiving cavity such that the two charger contacts provided at the bottom of the brush receiving cavity electrically connect with the two recharging contacts of the bottom cap assembly and the hanger hook is positioned through the hook slot; the elongated gripping portion housing a rechargeable battery pack in electrical connection with the pair of spaced recharging contacts and a reminder mechanism including a sealed output speaker, a sealed microphone, a user insertable electronic music chip insertable through a chip insertion opening formed through the side of the elongated gripping portion, an on/off switch and a music generating circuit having a speaker output in connection with the output speaker, a power input in connection the on/off switch, a sound detector microphone input in connection with the microphone, and a sound data input in connection with the user insertable electronic music chip; the music generating circuit retrieving sound data from the user insertable electronic music chip and generating a music output signal to the speaker after a predetermined sound is detected at the sound detector microphone input.

FIG. 1 shows an exemplary embodiment of the toothbrush with audible reminder mechanism of the present invention generally designated 10. Toothbrush with audible reminder mechanism 10 includes a brush assembly, generally designated 12, and a recharging base, generally designated 14. Recharging base 14 includes a brush assembly receiving cavity 16 having two charger contacts 18a, 18b provided at a bottom thereof and a hook slot 20 in connection with brush assembly receiving cavity 16.

Figure 2:
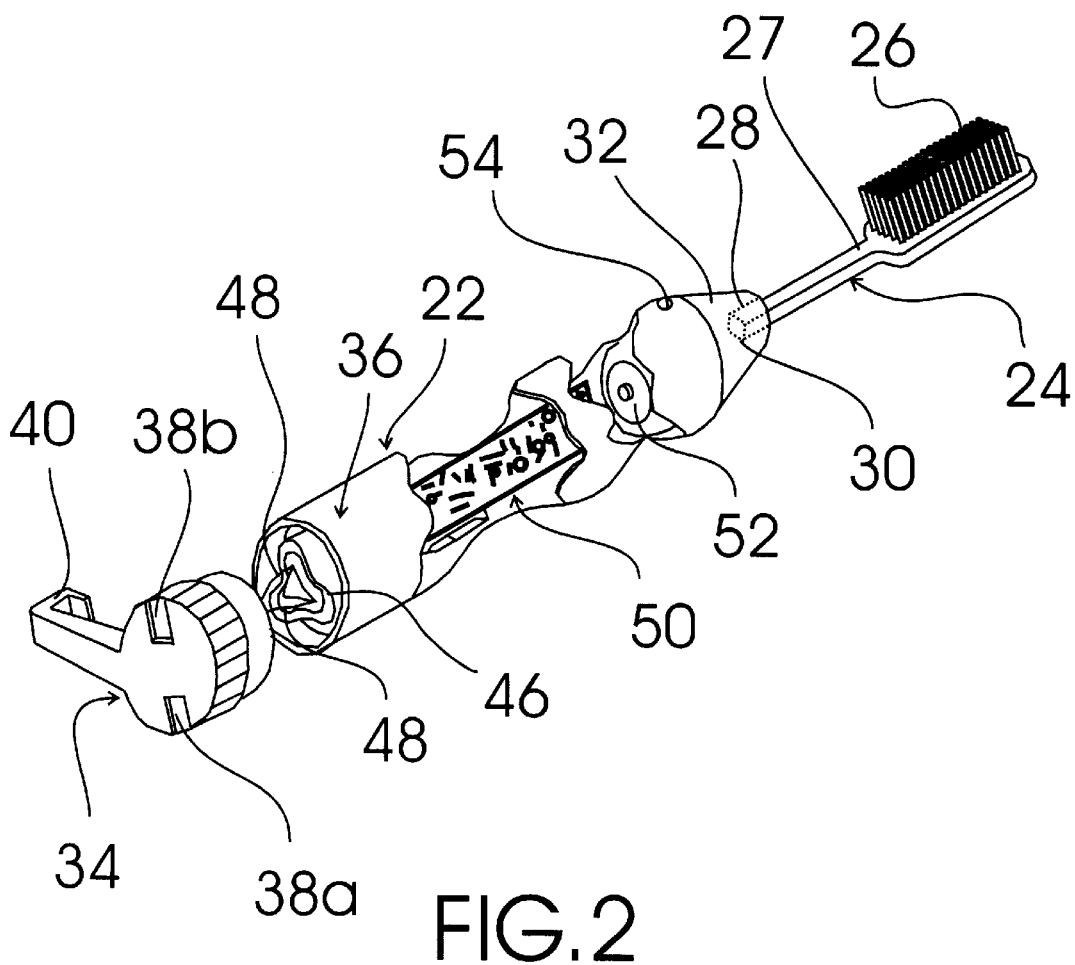
FIG. 2 is a partially exploded cutaway view of the brush assembly of FIG. 1 in isolation.

Brush assembly 12 includes a handle assembly, generally designated 22, and a removable brush assembly, generally designated 24, having a brush head 26 attached to a shaft portion 27 having, referring now to FIG. 2, a shaft end 28 that fits into a receiving cavity 30 at a top end 32 of handle assembly 22.

Handle assembly 22 includes a molded plastic housing having a detachable bottom cap assembly, generally designated 34, and a elongated gripping portion, generally designated 36. Detachable bottom cap assembly 34 is detachably connectable to elongated gripping portion 36 and includes a pair of spaced recharging contacts 38a, 38b and a hanger hook 40 extending out past a side of elongated gripping portion 36.

Elongated gripping portion 36 houses a rechargeable battery pack 46 in electrical connection with the pair of spaced recharging contacts 38a, 38b with connecting wires 48 and a reminder mechanism, generally designated 50. With reference also to FIG. 3, reminder mechanism 50 includes a sealed output speaker 52, a sealed microphone 54, a user insertable electronic music chip 56 (see also FIG. 1) insertable through a chip insertion opening 58 (FIG. 1) formed through the side of elongated gripping portion 36 and into a socket 60, an on/off switch 61 and a music generating circuit, generally designated 62. Music generating circuit 62 includes a speaker output 64 in connection with output speaker 52, a power input 66 in connection on/off switch 61, a sound detector microphone input 68 in connection with microphone 54, and a sound data input 70 in connection with user insertable electronic music chip 56 inserted in socket 60. Music generating circuit 62 retrieves sound data from user insertable electronic music chip 56 and generates a music output signal to speaker 52 after a predetermined sound, in this embodiment the sound of running water, is detected at sound detector microphone input 68.

It can be seen from the preceding description that a toothbrush with audible reminder mechanism has been provided that includes a brush assembly and a recharging base; the recharging base including a brush assembly receiving cavity having two charger contacts provided at the bottom thereof and a hook slot in connection with the brush assembly receiving cavity; the brush assembly including a handle assembly and a removable brush assembly having a brush head attached shaft portion having a shaft end that fits into a receiving cavity at a top end of the handle assembly; the handle assembly including a molded plastic housing having a detachable bottom cap assembly and a elongated gripping portion; the detachable bottom cap assembly being detachably connectable to the elongated gripping portion and including a pair of spaced recharging contacts and a hanger hook extending out past a side of the elongated gripping portion; the bottom cap assembly being insertable into the brush assembly receiving cavity such that the two charger contacts provided at the bottom of the brush receiving cavity electrically connect with the two recharging contacts of the bottom cap assembly and the hanger hook is positioned through the hook slot; the elongated gripping portion housing a rechargeable battery pack in electrical connection with the pair of spaced recharging contacts and a reminder mechanism including a sealed output speaker, a sealed microphone, a user insertable electronic music chip insertable through a chip insertion opening formed through the side of the elongated gripping portion, an on/off switch and a music generating circuit having a speaker output in connection with the output speaker, a power input in connection the on/off switch, a sound detector microphone input in connection with the microphone, and a sound data input in connection with the user insertable electronic music chip; the music generating circuit retrieving sound data from the user insertable electronic music chip and generating a music output signal to the speaker after a predetermined sound is detected at the sound detector microphone input.

It is noted that the embodiment of the toothbrush with audible reminder mechanism described herein in detail for exemplary purposes is of course subject to many different variations in structure, design, application and methodology.

Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A toothbrush with audible reminder mechanism comprising:

a brush assembly; and a recharging base;

said recharging base including a brush assembly receiving cavity having two charger contacts provided at a bottom thereof and a hook slot in connection with said brush assembly receiving cavity;

said brush assembly including a handle assembly and a removable brush assembly having a brush head attached shaft portion having a shaft end that fits into a receiving cavity at a top end of said handle assembly;

said handle assembly including a molded plastic housing having a detachable bottom cap assembly and a elongated gripping portion;

said detachable bottom cap assembly being detachably connectable to said elongated gripping portion and including a pair of spaced recharging contacts and a hanger hook extending out past a side of said elongated gripping portion;

said bottom cap assembly being insertable into said brush assembly receiving cavity such that said two charger contacts provided at said bottom of said brush receiving cavity electrically connect with said two recharging contacts of said bottom cap assembly and said hanger hook is positioned through said hook slot;

said elongated gripping portion housing a rechargeable battery pack in electrical connection with said pair of spaced recharging contacts and a reminder mechanism including a sealed output speaker, a sealed microphone, a user insertable electronic music chip insertable through a chip insertion opening formed through said side of said elongated gripping portion, an on/off switch and a music generating circuit having a speaker output in connection with said output speaker, a power input in connection said on/off switch, a sound detector microphone input in connection with said microphone, and a sound data input in connection with said user insertable electronic music chip;

said music generating circuit retrieving sound data from said user insertable electronic music chip and generating a music output signal to said speaker after a predetermined sound is detected at said sound detector microphone input.

* * * * *